(12) United States Patent
Yutaka et al.

(10) Patent No.: US 8,242,292 B2
(45) Date of Patent: Aug. 14, 2012

(54) METHOD OF PRODUCING 2,5-FURANDICARBOXYLIC ACID

(75) Inventors: Kie Yutaka, Saitama (JP); Toshinari Miura, Kawasaki (JP); Shinji Eritate, Kawasaki (JP); Takeshi Komuro, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/893,086

(22) Filed: Sep. 29, 2010

(65) Prior Publication Data

US 2011/0092720 A1 Apr. 21, 2011

(30) Foreign Application Priority Data

Oct. 19, 2009 (JP) ................................. 2009-240719

(51) Int. Cl.
*C07D 307/68* (2006.01)
(52) U.S. Cl. ...................................................... 549/485
(58) Field of Classification Search ........................ None
See application file for complete search history.

(56) References Cited

U.S. PATENT DOCUMENTS 7,019,024 B2 *  3/2006  Ognyanov et al. ............ 514/438
7,411,078 B2     8/2008  Miura et al.
2003/0055271 A1  3/2003  Grushin et al.
2010/0174044 A1  7/2010  Eritate

FOREIGN PATENT DOCUMENTS

| JP | 2003-528868 A | 9/2003 |
| WO | 01/72732 A2 | 10/2001 |

OTHER PUBLICATIONS

W. Partenheimer, Methodology & Scope of Metal/Bromide Autoxidation of Hydrocarbons, 23 Catalysis Today 69-158 (1995).*
Walt Partenheimer et al., "Synthesis of 2,5-Diformylfuran and Furan-2,5-Dicarboxylic Acid by Catalytic Air-Oxidation of 5-Hydroxymethylfurtural. Unexpectedly Selective Aerobic Oxidation of Benzyl Alcohol to Benzaldehyde with Metal/Bromide Catalysts," 343(1) Adv. Synth. Catal. 102-111 (2000).

* cited by examiner

*Primary Examiner* — Janet Andres
*Assistant Examiner* — Timothy R Rozof
(74) *Attorney, Agent, or Firm* — Fitzpatrick, Cella, Harper & Scinto

(57) ABSTRACT

Provided is a method of producing FDCA by which high-purity FDCA can be produced in high yield. 2,5-furandicarboxylic acid is produced by: bringing 5-hydroxymethylfurfural into contact with an oxidant in an organic acid solvent in the presence of bromine and a metal catalyst; and allowing 5-hydroxymethylfurfural and the oxidant to react with each other while removing water produced by the reaction.

7 Claims, 1 Drawing Sheet

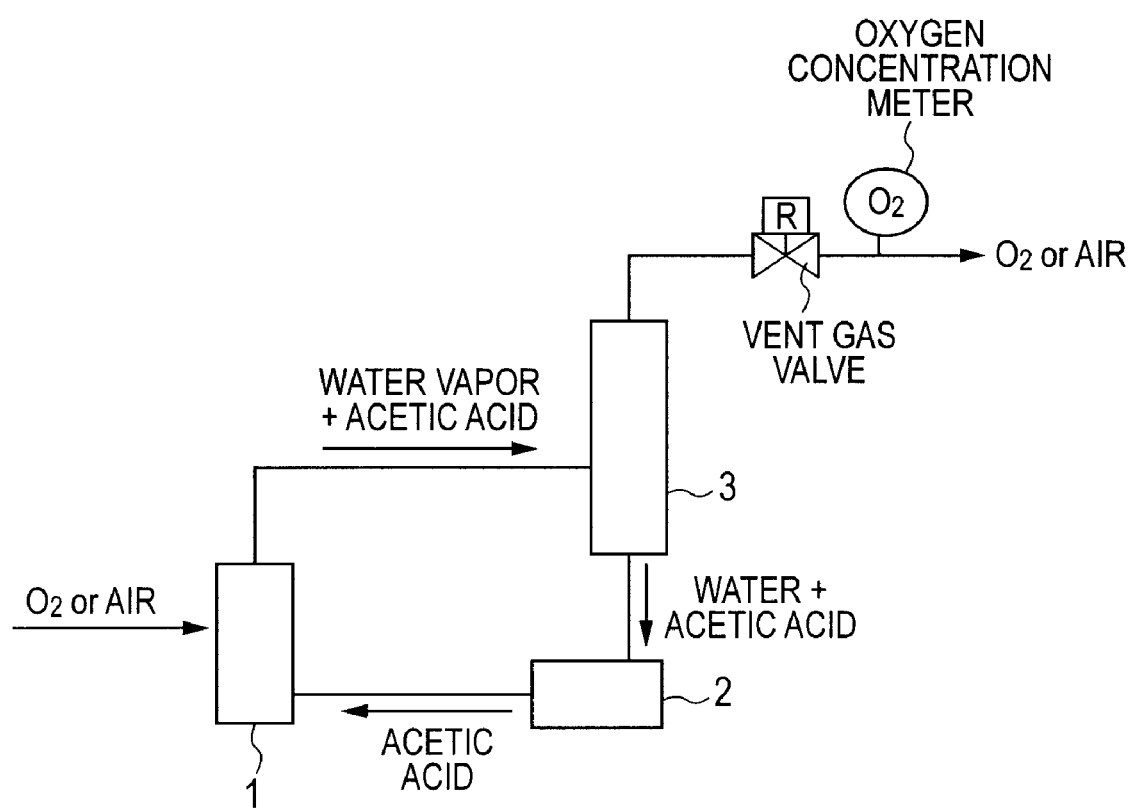

METHOD OF PRODUCING 2,5-FURANDICARBOXYLIC ACID

BACKGROUND OF THE INVENTION

1. Field of the Invention

The present invention relates to a method of producing 2,5-furandicarboxylic acid from 5 hydroxymethylfurfural.

2. Description of the Related Art

Investigations have been conducted on assorted methods of producing 2,5-furandicarboxylic acid (which may hereinafter be referred to as "FDCA") because the utilization value of FDCA as an intermediate in each of various fields including bioplastic monomers, drugs, agricultural chemicals, pesticides, antibacterial agents, flavors, and polymer materials is high. One of the methods is a method involving oxidizing 5-hydroxymethylfurfural (which may hereinafter be referred to as "5-HMF") in the presence of a catalyst to provide FDCA. 5-HMF can be obtained by dehydrating a hexose such as fructose or glucose, and is a useful compound that can be utilized as an intermediate for each of, for example, surfactants, plastics, and resins.

Japanese Patent Translation Publication No. 2003-528868 reports a method involving subjecting 5-HMF to air oxidation with a Co/Mn/Br catalyst in an acetic acid under a high-pressure condition to provide FDCA.

SUMMARY OF THE INVENTION

The yield in which FDCA is obtained by the method described in Japanese Patent Translation Publication No. 2003-528868 is low because the reaction occurs under such conditions that the concentration of the catalyst is high and a raw material concentration is low. The increase of the raw material concentration and an additional cost reduction are needed in order that the method may be proposed as an industrial production method. However, the increase of the raw material concentration is difficult to achieve with a conventionally known technology. Further, the development of a method by which FDCA is obtained with high purity and in high yield even under a high-concentration condition has also been requested.

The present invention has been made in view of such background art, and provides a novel method of producing FDCA by which high-purity FDCA can be produced in high yield.

In the present invention, attention is paid to water produced during a reaction, and the following method is provided. That is, a water content regulator is provided and a reaction is performed while a water content in a solvent is reduced, and hence FDCA can be produced in high yield and with high purity without any hindrance by water. According to the present invention, even when the concentration of a raw material is increased, FDCA can be produced in high yield and with high purity without any hindrance by water. In addition, the regulation of a water content in an organic acid solvent as a reaction solvent can be conducive to a cost reduction in an industrial production method because the deactivation of the catalyst by water can be prevented and hence the amount of the catalyst can be reduced.

A method of producing FDCA from 5-HMF for solving the above-mentioned problem is a method including: bringing 5-HMF into contact with an oxidant in an organic acid solvent in the presence of bromine and a metal catalyst; and allowing 5-HMF and the oxidant to react with each other to produce FDCA while removing water produced by the reaction.

The inventors of the present invention have paid attention to water produced during a reaction, and have found a method involving performing a reaction while reducing a water content in a solvent to produce FDCA with high purity and in high yield without any hindrance by water. According to the present invention, bioplastic monomers, drugs, agricultural chemicals, pesticides, antibacterial agents, flavors, and polymer materials can be stably supplied with high purity.

Further features of the present invention will become apparent from the following description of exemplary embodiments with reference to the attached drawing.

BRIEF DESCRIPTION OF THE DRAWINGS

FIGURE is a schematic view illustrating a production apparatus for producing FDCA according to an embodiment of the present invention.

DESCRIPTION OF THE EMBODIMENTS

Hereinafter, an embodiment of the present invention is described in detail with reference to FIGURE.

The inventors of the present invention have found that FDCA can be produced with high purity and in high yield by removing water produced during a reaction to regulate a water content in an organic acid solvent as a reaction solvent. That is, the present invention is characterized in that: 5-HMF is brought into contact with an oxidant in a reaction solvent in the presence of bromine and a metal catalyst; and 5-HMF and the oxidant are allowed to react with each other so that FDCA may be produced while water produced by the reaction is removed.

The phrase "removing water produced during a reaction" means not only "discharging water produced during a reaction to the outside of the reaction solvent" but also "allowing a dehydration agent in the reaction solvent to absorb water to prevent water produced during a reaction from adversely affecting the production reaction for FDCA." Adverse effects of water produced during the reaction on the production reaction for FDCA mean, for example, the production of a byproduct and the deactivation of the catalysts.

In the present invention, FDCA is produced with high purity and in high yield by regulating a water content in the reaction solvent to prevent the production of a byproduct and the deactivation of the catalysts due to water produced in the reaction solvent upon production of FDCA from 5-HMF.

The inventors of the present invention have found that FDCA can be obtained with high purity and in high yield by employing the above method of producing FDCA. The inventors have completed the present invention on the basis of such finding.

A method of removing water is, for example, a method involving removing water with a dehydration agent. Other methods of removing water include: a method involving allowing the reaction solvent such as an organic acid solvent containing water to evaporate to discharge the reaction solvent to the outside of a system, removing water from the vapor, and returning the reaction solvent to the system after the removal; a method involving the use of a filtration apparatus; and a method involving the utilization of separation.

In the case where water is removed by incorporating a dehydration agent into the solvent, water can be removed even when no unit for evaporating water is provided.

A method of evaporating the reaction solvent containing water involves keeping a pressure in a reaction vessel 1 lower than the vapor pressure of water for a reaction temperature to evaporate the reaction solvent containing water. In this case, the reaction temperature is preferably 200° C. or less, or more preferably 140° C. to 180° C. In addition, the reaction pressure is preferably 0.2 to 1.6 MPa, or more preferably 0.2 to 1.0 MPa.

By setting a reaction condition under which water evaporates, water in the reaction vessel 1 turns into water vapor. The water vapor is cooled by a cooling condenser 3 present in the midst of a reaction path to turn into water. The water is removed with a dehydration agent in a dehydrator 2 so that the reaction may be performed while the water content in the reaction solvent is regulated to 1.3% or less. Then, FDCA is produced in high yield.

In the above method, the presence of a water content regulator reduces factors that hinder the reaction such as an increase in amount in which a byproduct is produced and the deactivation of the catalysts. As a result, FDCA can be produced at a low cost, with high purity, and in high yield.

A product obtained by transforming a biomass such as cellulose, glucose, fructose, or mucic acid by a known method can be used as 5-HMF having a furan ring.

Bromine and the metal catalyst are used as the catalysts.

The metal catalyst preferably contains Co or Mn, or more preferably contains Co and Mn.

Br serves as an initiator for the reaction, and serves to advance the reaction while reducing Co as a main oxidation catalyst through ion discharge. Meanwhile, Co is known to be a main oxidation catalyst and the role of Mn is known to be an auxiliary catalyst for Co, and hence FDCA can be obtained in high yield with small amounts of the catalysts by optimizing a catalyst ratio between Co and Mn.

The reaction is preferably performed with such catalyst amounts that the content of Co is 0.50 to 5.0 wt %, the content of Mn is 0.15 to 3.0 wt %, and the content of Br is 0.11 to 3.2 wt % with respect to the raw material. In view of cost effectiveness as an industrial production method, the amount of Co as a catalyst having a high unit price can be suppressed to a low level by investigating an optimum catalyst ratio among Co, Mn, and Br. When catalyst ranges are set in view of a cost based on the total catalyst amount and the yield, it is more preferred that the content of Co be 0.50 to 1.0 wt %, the content of Mn be 1.5 to 2.3 wt %, and the content of Br be 0.32 to 3.2 wt %.

Oxygen and an oxygen-containing gas are each preferably used as the oxidant, and specific examples of the oxidant include, but not necessarily limited to, air, pure air, and a pure oxygen gas.

The above method can be performed in a solvent containing acetic acid or a solvent mixture.

Hereinafter, the present invention is described in detail by way of examples. However, the examples do not limit the present invention.

In each example, a raw material, catalysts, and a solvent were loaded into a reaction vessel provided with a stirring machine, and a reaction was initiated by bringing the raw material into contact with an oxidant while pressurizing and stirring the mixture. In order that the raw material and the catalysts might be sufficiently dissolved in the solvent before the reaction was initiated, the mixture was first stirred at room temperature for 1 hour.

An influence of water produced during the reaction must be reduced in order that a high yield may be obtained in a high-concentration solution. This is intended for the prevention of a side reaction and the deactivation of the catalysts due to water. In view of the foregoing, the reaction vessel was provided with a water content regulator, and oxidation was performed while a water content in the reaction solvent was regulated to 1.3% or less.

A temperature after a temperature increase is preferably a temperature equal to or less than 200° C. that is the decomposition temperature of 5-HMF. In consideration of a reaction time and reaction efficiency, the temperature is more preferably 140° C. to 180° C. A pressure in the reaction vessel is preferably set to be lower than the vapor pressure of water for the set temperature in order that water in the solvent may sufficiently dissipate. To be specific, the pressure is preferably 0.2 to 1.6 MPa, or more preferably 0.2 to 1.0 MPa.

In addition, FDCA produced by the reaction was filtrated so as to be separated into a liquid and a solid. The solid was sufficiently washed with water, and was then dried. After that, the yield of FDCA was measured by high-performance liquid chromatography (HPLC), and the water content in the reaction solvent was measured by Karl Fischer's method. Conditions for each measurement are shown below.

| HPLC measurement | |
| --- | --- |
| Analytical instrument: | 2695 manufactured by Waters |
| Detector: | A UV absorbance detector and a reflection detector |
| Eluent: | 3 mM of perchloric acid $HClO_4$ |
| Flow rate: | 1 ml/min |
| Column temperature: | 40° C. |
| Column: | SHODEX SUGAR SH-1011/SH-G manufactured by SHOKO CO., LTD. |

| Karl Fischer measurement | |
| --- | --- |
| Analytical instrument: | MKA-210 manufactured by KYOTO ELECTRONICS MANUFACTURING CO., LTD. |
| Solvent: | HAYASHI-solvent anhydrated solvent |
| Titrant: | HYDRANAL Composite 2 manufactured by Sigma-Aldrich Japan |

EXAMPLE 1

A catalyst-suspended aqueous solution prepared by weighing 45.5 ml of acetic acid, 4.8 g of 5-HMF, 0.10 g of cobalt acetate tetrahydrate, 0.32 g of manganese acetate tetrahydrate, and 0.010 g of sodium bromide was charged into the reaction vessel 1 (see FIGURE) provided with a stirring machine. In addition, the reaction vessel 1 was provided with a trap of 30 g of a Molecular Sieve (4A) manufactured by KISHIDA CHEMICAL Co., Ltd. as a water content regulator.

The prepared catalyst-suspended aqueous solution was stirred at 25° C. for 1 hour while air was introduced under a pressure of 0.3 MPa. After that, the temperature was increased to 150° C., and then stirring was performed for 1 hour in order that water might be sufficiently adsorbed by the dehydration agent of the trap. After that, the pressure was increased to 3 MPa, and then stirring was performed for 1 hour. Next, the temperature was reduced to 25° C., and then the product was taken out.

The product that had been taken out was filtrated. After that, quantitative determination by HPLC and water content measurement by Karl Fischer's method were performed. As a result, the yield of FDCA was 70.4% and a water content was 1.16%. A water content before the reaction was 0.023%.

EXAMPLE 2

A catalyst-suspended aqueous solution was prepared in the same manner as in Example 1 by weighing the same amounts of the samples as those of Example 1. The prepared catalyst-suspended aqueous solution was stirred at 25° C. for 1 hour while oxygen was introduced under a pressure of 0.3 MPa. After that, the temperature was increased to 150° C., and then stirring was performed for 2 hours while water was removed. Next, the temperature was reduced to 25° C., and then the product was taken out.

After the reaction, the same analysis as that of Example 1 was performed. As a result, the yield of FDCA was 73.4% and a water content was 1.03%.

EXAMPLE 3

A catalyst-suspended aqueous solution was prepared in the same manner as in Example 1 by weighing the same amounts of the samples as those of Example 1. The prepared catalyst-suspended aqueous solution was stirred at 25° C. for 1 hour while oxygen was introduced under a pressure of 0.3 MPa. After that, the temperature was increased to 150° C., and then stirring was performed for 2 hours. Next, the temperature was reduced to 25° C., and then the product was taken out.

After the reaction, the same analysis as that of Example 1 was performed. As a result, the yield of FDCA was 65.7% and a water content was 1.31%.

EXAMPLE 4

A catalyst-suspended aqueous solution was prepared in the same manner as in Example 1 by weighing the same amounts of the samples as those of Example 1. The prepared catalyst-suspended aqueous solution was stirred at 25° C. for 1 hour while oxygen was introduced under a pressure of 0.2 MPa. After that, the temperature was increased to 140° C., and then stirring was performed for 3 hours. Next, the temperature was reduced to 25° C., and then the product was taken out.

After the reaction, the same analysis as that of Example 1 was performed. As a result, the yield of FDCA was 68.0% and a water content was 1.02%.

EXAMPLE 5

A catalyst-suspended aqueous solution was prepared in the same manner as in Example 1 by weighing the same amounts of the samples as those of Example 1. The prepared catalyst-suspended aqueous solution was stirred at 25° C. for 1 hour while oxygen was introduced under a pressure of 0.4 MPa. After that, the temperature was increased to 155° C., and then stirring was performed for 2 hours. Next, the temperature was reduced to 25° C., and then the product was taken out.

After the reaction, the same analysis as that of Example 1 was performed. As a result, the yield of FDCA was 67.8% and a water content was 1.06%.

EXAMPLE 6

A catalyst-suspended aqueous solution was prepared in the same manner as in Example 1 by weighing the same amounts of the samples as those of Example 1. The prepared catalyst-suspended aqueous solution was stirred at 25° C. for 1 hour while oxygen was introduced under a pressure of 0.5 MPa. After that, the temperature was increased to 160° C., and then stirring was performed for 2 hours. Next, the temperature was reduced to 25° C., and then the product was taken out.

After the reaction, the same analysis as that of Example 1 was performed. As a result, the yield of FDCA was 65.8% and a water content was 1.11%.

EXAMPLE 7

A catalyst-suspended aqueous solution was prepared in the same manner as in Example 1 by weighing the same amounts of the samples as those of Example 1. The prepared catalyst-suspended aqueous solution was stirred at 25° C. for 1 hour while oxygen was introduced under a pressure of 0.6 MPa. After that, the temperature was increased to 165° C., and then stirring was performed for 2 hours. Next, the temperature was reduced to 25° C., and then the product was taken out.

After the reaction, the same analysis as that of Example 1 was performed. As a result, the yield of FDCA was 63.7% and a water content was 1.08%.

EXAMPLE 8

A catalyst-suspended aqueous solution was prepared in the same manner as in Example 1 by weighing the same amounts of the samples as those of Example 1. The prepared catalyst-suspended aqueous solution was stirred at 25° C. for 1 hour while oxygen was introduced under a pressure of 0.8 MPa. After that, the temperature was increased to 170° C., and then stirring was performed for 1 hour. Next, the temperature was reduced to 25° C., and then the product was taken out.

After the reaction, the same analysis as that of Example 1 was performed. As a result, the yield of FDCA was 65.4% and a water content was 1.09%.

EXAMPLE 9

A catalyst-suspended aqueous solution was prepared in the same manner as in Example 1 by weighing the same amounts of the samples as those of Example 1. The prepared catalyst-suspended aqueous solution was stirred at 25° C. for 1 hour while oxygen was introduced under a pressure of 1.0 MPa. After that, the temperature was increased to 180° C., and then stirring was performed for 1 hour. Next, the temperature was reduced to 25° C., and then the product was taken out.

After the reaction, the same analysis as that of Example 1 was performed. As a result, the yield of FDCA was 62.5% and a water content was 1.08%.

COMPARATIVE EXAMPLE 1

A catalyst-suspended aqueous solution was prepared in the same manner as in Example 1 by weighing the same amounts of the samples as those of Example 1. The catalyst-suspended aqueous solution was stirred at 25° C. for 1 hour while air was introduced under a pressure of 0.3 MPa. After that, the temperature was increased to 150° C., and then stirring was performed for 1 hour. After 1 hour, the pressure was increased to 3 MPa, and then stirring was performed for 1 hour. Next, the temperature was reduced to 25° C., and then the product was taken out.

After the reaction, the same analysis as that of Example 1 was performed. As a result, the yield of FDCA was 55.1% and a water content was 2.20%.

Comparative Example 2

A catalyst-suspended aqueous solution was prepared in the same manner as in Example 1 by weighing the same amounts of the samples as those of Example 1. The catalyst-suspended aqueous solution was stirred at 25° C. for 1 hour while oxygen was introduced under a pressure of 0.3 MPa. After that, the temperature was increased to 150° C., and then stirring was performed for 2 hours. Next, the temperature was reduced to 25° C., and then the product was taken out.

After the reaction, the same analysis as that of Example 1 was performed. As a result, the yield of FDCA was 52.2% and a water content was 1.71%.

COMPARATIVE EXAMPLE 3

A catalyst-suspended aqueous solution was prepared in the same manner as in Example 1 by weighing the same amounts of the samples as those of Example 1. The catalyst-suspended aqueous solution was stirred at 25° C. for 1 hour while air was introduced under a pressure of 3 MPa. After that, the temperature was increased to 150° C., and then stirring was performed for 2 hours. Next, the temperature was reduced to 25° C., and then the product was taken out.

Table 1 shows the results of the molecular weight measurement of Examples 1 to 9 and Comparative Examples 1 to 5.

TABLE 1

|  | Reaction temperature | Reaction time | Pressure | Oxidant | Dehydration agent | Water content (%) | Yield (%) FDCA |
|---|---|---|---|---|---|---|---|
| Example 1 | 150 | 3 h | 0.3→3 | Air | Present | 1.16 | 73.4 |
| Example 2 | 150 | 3 h | 0.3 | Oxygen | Present | 1.03 | 70.4 |
| Example 3 | 150 | 3 h | 0.3 | Oxygen | Present | 1.31 | 65.7 |
| Example 4 | 140 | 4 h | 0.2 | Oxygen | Present | 1.02 | 68.0 |
| Example 5 | 155 | 3 h | 0.4 | Oxygen | Present | 1.06 | 67.8 |
| Example 6 | 160 | 3 h | 0.5 | Oxygen | Present | 1.11 | 65.8 |
| Example 7 | 165 | 3 h | 0.6 | Oxygen | Present | 1.08 | 63.7 |
| Example 8 | 170 | 2 h | 0.8 | Oxygen | Present | 1.09 | 65.4 |
| Example 9 | 180 | 2 h | 1.0 | Oxygen | Present | 1.08 | 62.5 |
| Comparative Example 1 | 150 | 3 h | 0.3→3 | Air | Absent | 2.20 | 55.1 |
| Comparative Example 2 | 150 | 3 h | 0.3 | Oxygen | Absent | 1.71 | 52.2 |
| Comparative Example 3 | 150 | 3 h | 3 | Air | Present | 1.64 | 57.6 |
| Comparative Example 4 | 150 | 3 h | 3 | Air | Absent | 1.72 | 52.3 |
| Comparative Example 5 | 150 | 3 h | 3 | Air | Absent | 2.36 | 40.2 |

After the reaction, the same analysis as that of Example 1 was performed. As a result, the yield of FDCA was 57.6% and a water content was 1.64%.

COMPARATIVE EXAMPLE 4

A catalyst-suspended aqueous solution was prepared in the same manner as in Example 1 by weighing the same amounts of the samples as those of Example 1. The catalyst-suspended aqueous solution was stirred at 25° C. for 1 hour while air was introduced under a pressure of 3 MPa. After that, the temperature was increased to 150° C., and then stirring was performed for 2 hours. Next, the temperature was reduced to 25° C., and then the product was taken out.

After the reaction, the same analysis as that of Example 1 was performed. As a result, the yield of FDCA was 52.3% and a water content was 1.72%.

COMPARATIVE EXAMPLE 5

A catalyst-suspended aqueous solution was prepared as a trace experiment of the prior art with the same raw material concentration as that of Example 1 by weighing catalysts so that the concentrations of the catalysts might be equal to those of a prior example described in Walt Partenheimer, Vladimir V. Grushin Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts Advanced Synthesis & Catalysis. WILEY-VCH Verlag Gmbll, 69451 Weinheim, 2000, No. 1, p 102-111. To be specific, the preparation was performed by adding 0.031 g of Co, 0.029 g of Mn, and 0.082 g of Br.

The catalyst-suspended aqueous solution was stirred at 25° C. for 1 hour while air was introduced under a pressure of 3 MPa. After that, the temperature was increased to 150° C., and then stirring was performed for 2 hours. Next, the temperature was reduced to 25° C., and then the product was taken out.

After the reaction, the same analysis as that of Example 1 was performed. As a result, the yield of FDCA was 40.2% and a water content was 2.36%.

Summary of Experimental Results

It was found that a yield of FDCA of 62% or more was attained by: setting the pressure to a value lower than the vapor pressure of water for a reaction temperature; providing the step of removing water with a dehydration agent; and performing the reaction under such a condition that the water content in the reaction solvent was 1.3% or less.

It should be noted that the vapor pressures of water at the respective temperatures are as shown below.

| | |
|---|---|
| 140° C. | 0.37 MPa |
| 150° C. | 0.49 MPa |
| 155° C. | 0.56 MPa |
| 160° C. | 0.64 MPa |
| 165° C. | 0.73 MPa |
| 170° C. | 0.82 MPa |
| 180° C. | 1.05 MPa |

In addition, the yield of FDCA was 40.2% in Comparative Example 5 as an example in which the reaction was performed with the catalyst amounts of Partenheimer et al. The yield was lower than the yield of FDCA described in the document, i.e., 60.9%. The foregoing showed that a higher yield of FDCA was attained by the catalyst ratio reported in the present invention than by the prior art.

INDUSTRIAL APPLICABILITY

According to the method of producing FDCA of the present invention, an intermediate in each of various fields including bioplastic monomers, drugs, agricultural chemicals, pesticides, antibacterial agents, flavors, and polymer materials can be stably supplied with high purity.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-240719, filed Oct. 19, 2009, which is hereby incorporated by reference herein in its entirety.

What is claimed is:

1. A method of producing 2,5-furandicarboxylic acid, the method comprising:
    bringing 5-hydroxymethylfurfural into contact with an oxidant in an organic acid solvent in the presence of bromine and a metal catalyst; and
    allowing 5-hydroxymethylfurfural and the oxidant to react with each other while removing water produced by the reaction to produce 2,5-furandicarboxylic acid,
    wherein the water is removed in an evaporated form,
    wherein the metal catalyst is cobalt (Co) and manganese (Mn), and
    wherein a content of Co is 0.50 to 1.0 wt % and a content of Mn is 0.15 to 2.3 wt % with respect to raw material.

2. A method of producing 2,5-furandicarboxylic acid according to claim 1, further comprising:
    evaporating the organic acid solvent containing the water to discharge the organic acid solvent to an outside of a system;
    removing the water from the vaporized organic acid solvent; and
    returning the organic acid solvent to the system after the removal.

3. A method of producing 2,5-furandicarboxylic acid according to claim 1, further comprising keeping a pressure lower than a vapor pressure of water for a reaction temperature to evaporate the organic acid solvent containing the water.

4. A method of producing 2,5-furandicarboxylic acid according to claim 1, wherein the organic acid solvent after completion of the reaction has a water content of 1.3% or less.

5. A method of producing 2,5-furandicarboxylic acid according to claim 1, wherein the oxidant comprises molecular oxygen.

6. A method of producing 2,5-furandicarboxylic acid according to claim 1, wherein the organic acid solvent comprises an acetic acid.

7. A method of producing 2,5-furandicarboxylic acid according to claim 1, wherein the reaction system comprises sodium bromide.

* * * * *